(12) United States Patent
Lingg

(10) Patent No.: US 8,406,863 B2
(45) Date of Patent: *Mar. 26, 2013

(54) DEVICE FOR USING SAVED FREQUENCY INFORMATION

(76) Inventor: Gerhard Lingg, Bregenz (AT)

( * ) Notice: Subject to any disclaimer, the term of this patent is extended or adjusted under 35 U.S.C. 154(b) by 667 days.

This patent is subject to a terminal disclaimer.

(21) Appl. No.: 12/522,212

(22) PCT Filed: Dec. 31, 2007

(86) PCT No.: PCT/EP2007/011479
§ 371 (c)(1),
(2), (4) Date: Aug. 19, 2009

(87) PCT Pub. No.: WO2008/083847
PCT Pub. Date: Jul. 17, 2008

(65) Prior Publication Data
US 2010/0004551 A1    Jan. 7, 2010

(30) Foreign Application Priority Data

Jan. 9, 2007 (AT) .................................. A 45/2007
Jun. 19, 2007 (AT) ................................ A 950/2007

(51) Int. Cl.
*A61N 1/00* (2006.01)

(52) U.S. Cl. ............................................ 600/519; 607/3
(58) Field of Classification Search .................. 600/519; 607/3
See application file for complete search history.

(56) References Cited

U.S. PATENT DOCUMENTS

| 6,029,084 A * | 2/2000 | Long et al. ................... 607/2 |
| 2005/0222625 A1 | 10/2005 | Laniado et al. ................ 607/2 |
| 2005/0239493 A1 * | 10/2005 | Batkin et al. ............... 455/550.1 |
| 2006/0224215 A1 | 10/2006 | Pattern et al. ................. 607/62 |

FOREIGN PATENT DOCUMENTS
WO    WO 2004/011091    2/2004

* cited by examiner

*Primary Examiner* — Eric D. Bertram
(74) *Attorney, Agent, or Firm* — Andrew Wilford

(57) ABSTRACT

The invention relates to a device for applying saved frequency information in the form of modulated magnetic fields and/or modulated light to the body, wherein the device comprises at least one transceiver, one display, one memory, one control electronic, one D/A-converter, and a coil (6) for the application of modulated magnetic fields and/or a laser (7) for the application of modulated light. The invention also relates to a method for tapping signals of the electric potential of the heart and the pulse value and applying saved frequency information by means of a device according to the invention.

15 Claims, 3 Drawing Sheets

DEVICE FOR USING SAVED FREQUENCY INFORMATION

CROSS REFERENCE TO RELATED APPLICATIONS

This application is the US national phase of PCT application PCT/EP2007/011479, filed 31 Dec. 2007, published 17 Jul. 2008 as WO2008/083847, and claiming the priority of Austrian patent application A45/2007 itself filed 9 Jan. 2007 and Austrian patent application A950/2007 itself filed 19 Jun. 2007, whose entire disclosures are herewith incorporated by reference.

The invention relates to a device for applying saved frequency information in the form of modulated magnetic fields and/or modulated light to the body.

It is known that the application of modulated magnetic fields and/or modulated light to the body can have different effects on its function. For example, bio-information can be recorded in the form of electromagnetic spectra and transmitted to the body with a respective device. Depending on the spectrum of the substance, the influence on the body can be different. There are, for example, spectra of substances which cause a strained body to calm down, or others, which are activating in the case of tiredness.

Applying the frequency information to the body can take place either without prior analysis of the current state of the user, or there can be made a state analysis by means of a heartrate-variability-heart-coherence-(HRV)-screening for the more precise selection of a suitable frequency. The HRV-screening is a non-invasive, by finger sensors recorded screening of the autonomous nervous heart regulation in the sense of a heartrate-variability-heart-coherence-analysis. This allows for hints on the overall state of the functioning of the autonomous nervous system. It enables statements about the strength of the sympathetic activity, the autonomous balance, and its shift in direction of a sympathetic or parasympathetic dominance, respectively, wherein these statements correlate with the metabolic regulation of the human organism and point to a catabolic or anabolic metabolism, respectively, and further enable to conduct a stress test which allows statements regarding the physical and mental stress.

It is known to save frequency information of organic substances on a computer and to transmit them on the body by means of a connected magnetic coil or modulatable light sources, respectively. A drawback of this is that the devices are large and therefore allow only a stationary use. The number of supported frequency information depends on the size of the memory of the device and it is not possible for the user to apply a respective frequency information or conduct a state analysis any time and anywhere. Furthermore, the state analysis by means of HRV-Screening for the selection of the proper frequency information and for its application requires different and sometimes bulky devices and substantial know-how, so that the usability is strongly reduced.

It is therefore a goal of the invention to create a handy and everywhere usable device which allows to apply an indefinite number of different frequency information to the body and which also allows to analyze the current state of the user by means of HRV-Screening.

This task is solved by the device which comprises at least one transceiver, a display, a memory, control electronics, a digital-analog converter and a coil for applying the modulated magnetic fields and/or a laser for applying modulated light. It is a characteristic of the invention, that the device is a cell phone which is equipped with a coil and/or a laser and a respective digital-analog converter.

A further characteristic of the invention is that the coil creates a magnetic field with a fluctuating frequency with a mean value of 9 Hz, wherein furthermore the magnetic field can be oriented symmetrically transverse to the longitudinal axis of the device. The strength of the magnetic field which is created by the coil can range from 0.1 up to 70 µTesla at a measuring distance of 0 m. The laser can be a semiconductor-laser-diode which creates light of a fluctuating red wave length with a mean value of 650 nm. The power of the laser is smaller than 1 mW, preferably around 0.5 mW at around 15 mW/cm$^2$.

A further characteristic of the invention is that the frequency information which shall be used can be downloaded with the transceiver from a server, stored in the memory of the device, and transmitted to the coil and/or the laser via the digital-analog converter. For this, the frequency information to be used is represented by a digital file format, for example a digital audio file. Therefore, a substantial advantage of the invented device is, that an indefinite number of different frequency information can be stored on the server and can be downloaded by means of the transceiver every time and everywhere and can be applied to the body by means of the coil or the laser, respectively.

It is further a characteristic of the invention that the device comprises at least two, preferably three sensors for measuring the electric potential of the heart and at least one sensor, preferably in form of a phototransistor, for measuring the pulse. In one embodiment, three metal sensors in form of electrodes, for example made of plastic bodies that are coated with Ag/AgCl and a photo sensor can be provided, each located around the edge points of a cell phone, wherein each sensor is touched by one finger of the user.

The control electronic of the device processes the signals received from the sensors and computes a heartrate-variability-heart-coherence-analysis and finally shows the result on the display of the device.

As a further characteristic of the invention, the control electronic can compare the computed result with a database in the memory of the device, and can show on the display of the device a respective selection of applicable frequency information, as well as further information, wherein the shown applicable frequency information is downloadable from a server by means of the transceiver.

In a further possible embodiment, the sensors, the memory, the control electronic, the digital-analog converter, as well as the coil and/or the laser of the device are provided in a common module, which can be connected to the cell phone or can be built into it. The module can further comprise its own current supply, for example an accumulator. For the communication between the module and the cell phone it can be equipped with an interface, for example a Bluetooth and/or USB-interface.

The invention also relates to a method for tapping signals of the electric potential of the heart and the pulse value and using the frequency information in the form of modulated magnetic fields and/or modulated light on the body by means of a device according to the described invention wherein the method comprises the following steps:

Recording the signals via three or four sensors at the device, wherein preferably one sensor is a photo transistor and the other sensors are suited for the tapping of electric signals. Creation of a heartrate-variability-heart-coherence-analysis by means of the device. Comparing the computed result with a database in the device, where the database has stored respective information for different results, like, for example, nutrition suggestions or suggestions of possible applicable frequency information. Showing the computed results, as well as the respective database entries, on a display of the device. The optional, user-controlled downloading of the respective displayed frequency information by the user from a server, and the transmission onto the device by means of the transceiver. Conversion of the transmitted frequency information by means of the digital-analog converter into an analog frequency. Application of the analog frequency to the body by means of a coil and/or the laser of the device, and an optional further recording and creation of a heartrate-variability-heart-coherence-analysis for checking the state change of the user.

Below, the invention will be explained in more detail using several figures and the respective description, wherein FIG. 1 is a schematic front view of a device according to the invention in form of a cell phone.

Figure 1:
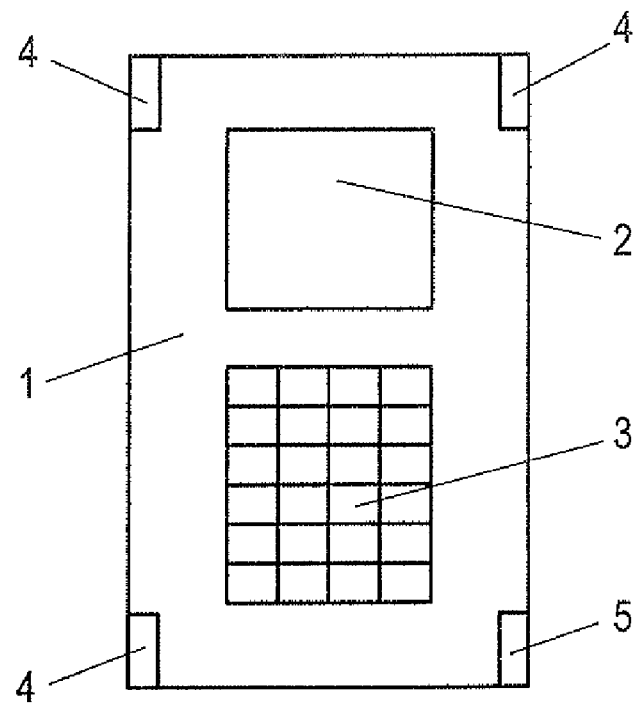

The cell phone 1 schematically shown in FIG. 1 with a display 2 and a keyboard 3 comprises at each of its edges a sensor to receive a finger of the user. For this, three metal sensors 4 for recording an EKG, as well as a photo sensor 5 to recognize the pulse wave are provided. The user can hold the cell phone with both hands and one finger at each edge point during the recording of the signals.

Figure 2:
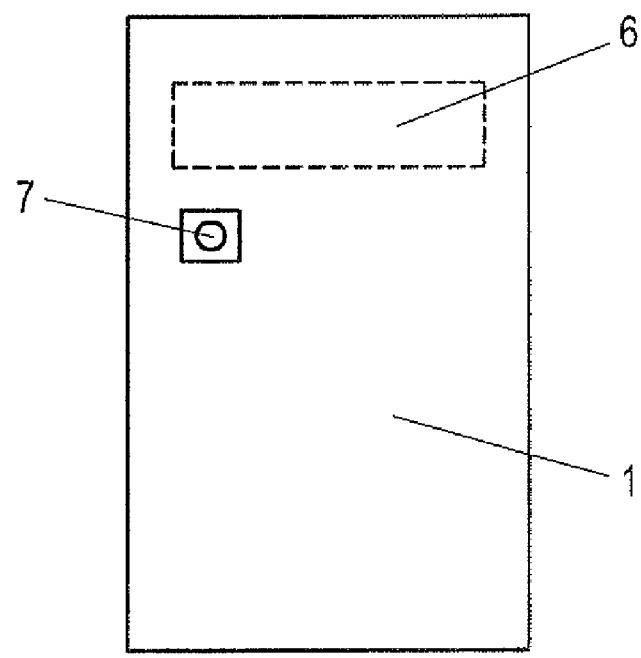
FIG. 2 is a back view of the device according to the invention shown in FIG. 1.

FIG. 2 shows the back view of the cell phone of FIG. 1. The dashed lines show the coil 6 serving for the application of the modulated magnetic fields, which is located in the case and not visible from the outside. In this embodiment, there is further at the back side of the cell phone a laser 7, which serves for the application of the modulated light to the body. The laser 7 can, of course, also be arranged at a different, suitable location. After confirming the state of the user by means of the four sensors 4, 5, and subsequent computation of the heartrate-variability, and after a respective frequency information has been suggested and downloaded from the server, the cell phone 1 can be laid on the skin with its back side, and the frequency information can be applied as a modulated magnetic field or modulated light, respectively.

Figure 3:
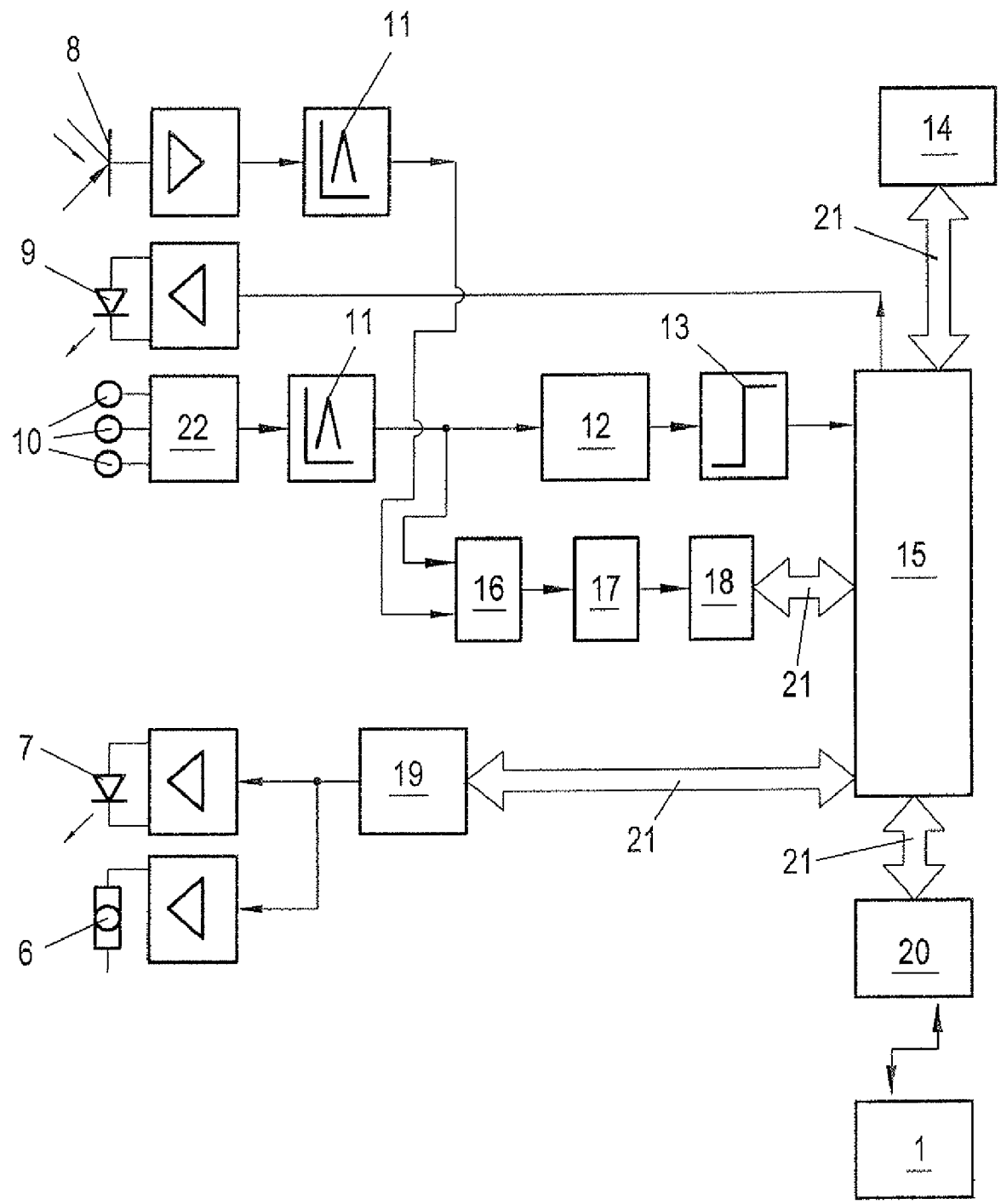
FIG. 3 shows a block diagram of a possible embodiment of the device according to the invention.

The functioning of the device is now explained in more detail using the block diagram shown in FIG. 3.

The basic functions of the shown embodiment, as well as the application sequence, are:

The analysis of the state of the user, based on a HRV-Analysis and a pulse wave correlation Suggestions for frequency information as well as further suggestions for the change of the state of the user, queried from the database of the device Downloading of an adequate frequency information via the transceiver Application of the frequency information to the user via a magnetic field and a modulated laser light Checking the state change by repeating the HRV-Analysis and pulse wave correlation.

Analysis of the State of the User:

A 1-channel-EKG, which is tapped via three finger-electrodes 10, is recorded. A differential amplifier 22 with high impedance and satisfactory common mode rejection amplifies the source-signal with an amplitude of around 1-2 mV to around 500 mV and cuts off DC-parts, which might eventually emerge by electrochemical creation of elements between the skin and the electrode surface. A subsequent filter 11 cuts off the 50 Hz line noise. The so-conditioned signal passes a multiplexer 16 and a sample&hold 17 and goes to an ADC 18. This samples the EKG-signal with a sample rate of 2 ms=500 Hz. The control of the AD-conversion is done by a central RISC-processor 15, which also transfers the data from the ADC 18 to the buffer-RAM 14. Its stored data is transmitted on request of the cell phone 1 via the Bluetooth-interface 20. In parallel to this EKG-recording, a special, on analogue technology based R-ware-detection 12 with subsequent trigger 13 and subsequent computation of the reciprocal value in the processor 15 is performed, and a direct RR-value is computed and stored in the RAM 14 as well. These values are also transmitted per request of the cell phone 1. The measuring accuracy of the sensors is +/−6%.

Since a processor 15 is required for the application anyway, signal-preprocessing and filtering is implemented in software. Next to the saving of comparably expensive external analog hardware, this has the advantage of adaptability, for example for 50 Hz/60 Hz line noise-filtering as well as easier maintenance. With this, later improvements can be installed via firmware-update by the user. Since the measured data cannot be transmitted fast enough to the cell phone over the interface (Bluetooth), it is necessary to buffer the stream of measured data in an external RAM 14 which is attached to the processor. Eventually, a slower flash-memory, which typically uses less energy, can be used as a RAM.

During application, frequency information shall be delivered to the user by the device via different, optical and/or magnetical, actors. For this, the RAM, which has been used for the buffering of the measured data, is used again, because the signal data must be transmitted from the interface to the cell phone and must be buffered, before it can be transmitted as a data stream via the preceding DAC 19 to the actors 6, 7. It is also possible to implement a closed-loop control for the user, in which a "realtime-bio-feedback-control-loop" for the instantaneous measurement of EKG- and pulse data and the application of frequency information can be built up.

As electrode material, a plastic body coated with Ag/AgCl is suggested. This material features an optimum value of the electrochemical voltage, so that a quick discharging of emerging DC-voltages is possible. An alternative would be electrodes which are coated with noble metals such as AU-coated electrodes.

Via an IR-light barrier, consisting of an IR-LED 9 and a photo transistor 8, the pulse wave is detected on a fingertip. The recorded signal is filtered and goes via the second channel of the multiplexer 16 and the S&H 17 also to the ADC 18. By alternating AD-conversion between EKG and PW, a temporal correlation of values (within the frame of the sampling rate) is given.

To minimize the current consumption, the IR-LED 9 can be turned on when a R-wave is detected, and turned off again, when a pulse wave is detected.

From the available frequency components, both the strength of the sympathetic and parasympathetic activity, and the heart-rhythm-coherence-ratio can be determined by means of high-accuracy integration of special frequency domains.

Both branches of the autonomous nervous system, the sympathetic and the parasympathetic nervous system, work independent of each other and, usually, antagonistic. The sympathetic nervous system induces willingness to perform and causes stress when over-activated. The parasympathetic nervous system, on the other hand, has a dampening and relaxing effect on the organism, supporting the regeneration and preventing from over-activation by stress.

The relative strength of the sympathetic and parasympathetic nervous system activation can be different for each human. Both subsystems should normally be in a state of balance. In a lot of cases, however, there is a dominance of one or the other system. A statement about the condition of the autonomous balance is possible, in particular, by the ratio of sympathetic to parasympathetic activation possible.

A balance shift in direction to a sympathetic dominance is catabolic and causes supply of energy to increase the performance by different metabolic measures like blocking the energy storage and dissolving existing energy storage, like for example protein breakdown, raise of the blood sugar level, or an increase in free fatty acids. Furthermore it forces the energy transport by hematological (reduction of the plasma volume, increase of the hemoconcentration and cardiovascular (increase of the blood pressure, increase of the heart contractility, reduction of the nervous conduction time in the heart) measures, and blocks irrelevant or not helpful body processes, like for example digestive processes, reproductive processes, growth processes and anabolism, inflammatory reactions, pain sensitivity and immunoreactivity. A balance shift in direction of a parasympathetic dominance acts in the opposite direction. It acts anabolic and fosters anabolism, relaxation, regeneration, reducing stress and protecting from stress-induced illnesses of the heart and other body organs.

The result which has been computed from the recorded signals is compared with a database which is stored in the memory of the device, and the following information for the user, depending on the measurement result, can be displayed:

The situation of the metabolism regulation, catabolic or anabolic, as well as respective nutrition suggestions The autonomous balance of the autonomous nervous system A stress check with a download suggestion for a proper applicable frequency information The result of the feedback coaching after application of a frequency information Further download suggestions for standard application Application of the Frequency Information The applicable frequency information has been loaded into the RAM of the cell phone via download from a server such as from a link of the cell phone provider. From there it is read from the processor 15 and over the 1-Bit-DAC 10 applied onto a magnetic coil 6 in combination with a strong static magnetic field. The core of this coil 6 will be structurally modified by the AMS-process. This coil creates field strengths of ca. 70 µT and influences the user. With the same frequency information signal, the brightness of a small power semiconductor laser-diode 7 with a power of less than 1 mW is modulated. This laser light also directly influences the user. The signals between the processor 15, the RAM 14, the ADC 18, the 16-Bit DAC 19, and the Bluetooth-interface 20 are transmitted over a SPI-Bus 21. The frequency information can further be applied via a infrared source 23.

Figure 4:
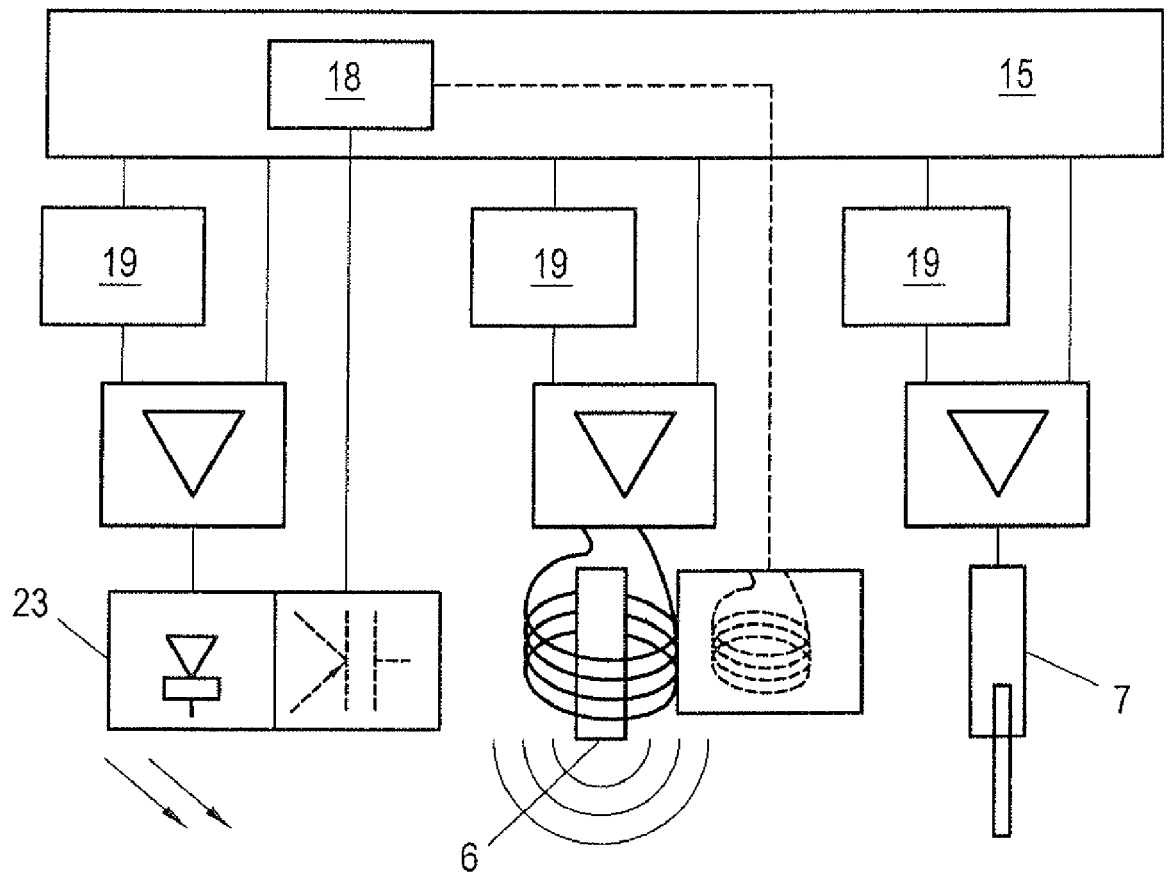
FIG. 4 shows a block diagram of a possible circuit for controlling the actors.

FIG. 4 shows a circuit variant for maximum flexibility in controlling the actors which apply the frequency information to the user. Each actor 6, 7, 23 has its own digital-analog converter 19 and its own preamplifier stage.

The processor has to fulfill the following tasks, in extreme cases all of them "simultaneously":

Queries from the interface to the cell phone

Control of the EKG-signal-windowing

Sampling the EKG- and pulse-signals

Preprocessing and filtering of the EKG- and pulse-signals

Buffering the EKG- and pulse-data in the RAM

Providing the EKG-/pulse-data stream for the transmission over the interface (Bluetooth/USB)

Restoring the frequency information buffered by the RAM over the channels to the actors For this the realization of a complex interrupt-handling mechanism is required. The simultaneous running of so many sub processes poses a particularly high development effort to achieve an optimum timing.

The choice of Bluetooth as a communication interface between the module and the cell phone is surely advantageous, since by this the adaption of different Bus-systems to varying "carrier-hardware" can be evaded in a clever way. Hence, the wiring between the cell phone unit and the module can be reduced to the energy supply. This is for example possible with just two contacts protected from corrosion. Alternatively, the current supply of the module can also be done separately, for example with a separate battery. By this, a 1-board-design is strived for, to keep the cost for series production as low as possible. On this circuit board all components of the module are disposed, including the sensors and the actors. Hence, the module can be laid or screwed or clipped very cost effectively into a modified back cover of the cell phone. Hence, no wiring is necessary for installation.

At the server there are for example 3000 different spectra digitally stored. Preferably, these frequency information spectra are available as digital audio files, for example as wave-sound files.

Substance spectra are recorded for around 4 min by placing them into an input coil to which a filter and an amplifier with an amplification of $10^6$ are connected. The electro-magnetic waves which are emitted by the substances with frequencies in the range of 20 Hz up to 100 kHz are digitized via the Nyguist-frequency, buffered into a RAM and transmitted to CD in a multiplex process. The noise-suppressed filtered signal is attenuated by $10^6$ to the original analog level. This signal is loaded onto a server and can be downloaded onto a device according to the invention.

During playback of the wave-sound file preferably the range of 20 Hz up to 18 kHz is considered and is applied via a coil (magnetic field) with a fluctuating frequency with a mean value of around 9 Hz by means of coherent light (laser). The harmonics reach up into the megahertz range, and in addition to this all frequencies of the geomagnetic field are created and transmitted. The direction of the magnetic field is symmetric transverse to the long middle axis of the device. The accuracy of the fixed frequencies lies around +/−0.2%. The magnetic field strength is, depending on the regulation, preferably from 0.17-3.8 µTesla at a measuring distance of 0 m. There can be an automatic shut off after 30 sec-3 min for all frequencies with an accuracy of around +/−1%.

The laser works with a fluctuating red wave length (mean value 650 nm). The power is ca. 0.5 mW, at ca. 15 mW/cm$^2$ in continuous use with the same duration as with the magnetic field. There is no pulsing.

The invention claimed is:

1. A device for applying frequency information saved in a server in the form of modulated magnetic fields and modulated light to the body, the device comprising:

at least one transceiver for downloading the saved frequency information from the server, one display, one memory connected to the transceiver for storing the downloaded frequency information, one electronic controller, one D/A-converter connected to the memory for receiving the downloaded frequency information therefrom, a coil connected to the D/A converter for applying magnetic fields modulated by the downloaded frequency information, a laser connected to the D/A converter for applying light modulated by the downloaded frequency information, two sensors for measuring the electrical potential of the heart of the body, and a phototransistor for measuring the pulse of the body.

2. The device as described in claim 1 wherein the device is a cell phone.

3. The device as described in claim 1 wherein the magnetic field of the coil has a fluctuating frequency with a mean value of 9 Hz.

4. The device as described in claim 1 wherein the magnetic field is oriented symmetric transverse to the longitudinal axis of the device.

5. The device as described in claim 1 wherein the magnetic field created by the coil has a magnetic field strength of 0.1 to 70 µT at a measuring distance of 0 m.

6. The device as described in claim 1 wherein the laser is a semiconductor laser-diode which creates light with a fluctuating red wave length with a mean value of 650 nm.

7. The device as described in claim 1 wherein the laser has a power of less than 1 mW.

8. The device as described in claim 1 wherein the frequency information to be applied is available in form of a digital file format.

9. The device as described in claim 1 wherein the sensors are metallic electrodes and the phototransistors and electrodes are each arranged near edges of a cell phone for the application of one finger to each sensor.

10. The device as described in claim 1 wherein the electronic controller of the device processes the signals received from the sensors for the computation of a heartrate-variability-heart-coherence-analysis and shows the result on the display.

11. The device as described in claim 10 wherein the result computed by the electronic controller is compared with a database in the memory of the device, and that on the display of the device a corresponding selection of applicable frequency information and additional further information can be shown, the shown selection of applicable frequency information being downloadable from the server by the transceiver.

12. The device as described in claim 1 wherein the sensors, the memory, the electronic controller, the D/A-converter, the coil or the laser are arranged in a common module connectable to a cell phone or built into the cell phone.

13. The device as described in claim 12 wherein the module further comprises its own current supply.

14. The device as described in claim 12 wherein the module is connectable to the cell phone by a Bluetooth or a USB interface.

15. A method for tapping signals of the electric potential of the heart and the pulse value and applying saved frequency information in form of modulated magnetic fields or modulated light to the body by means of a device according to claim 1, the method comprising the following steps:

recording the signals via the sensors on the device, wherein one sensor is the phototransistor and the other sensors are designed for the tapping of electrical signals;

creation of a heartrate-variability-heart-coherence-analysis;

comparing the computed result with a database in the device where the database has stored corresponding information for different results;

showing the computed results and the corresponding database entries on the display of the device;

conversion of the transmitted frequency information by means of the D/A-converter into an analog frequency; and application of the analog frequency to the body by means of the coil and the laser of the device.

\* \* \* \* \*